(12) United States Patent
Lange

(10) Patent No.: US 6,294,691 B1
(45) Date of Patent: Sep. 25, 2001

(54) PROCESS FOR THE MANUFACTURE OF CARBOXYLIC ACIDS

(76) Inventor: Jean-Paul Lange, Badhuisweg 3, 1031 CM Amsterdam (NL)

(*) Notice: Subject to any disclaimer, the term of this patent is extended or adjusted under 35 U.S.C. 154(b) by 0 days.

(21) Appl. No.: 09/102,983

(22) Filed: Jun. 22, 1998

(30) Foreign Application Priority Data

Jun. 20, 1997 (EP) .................................... 97201893

(51) Int. Cl.$^7$ ............................ C07C 51/14; C07C 51/10
(52) U.S. Cl. ........................................ 562/521; 562/519
(58) Field of Search ..................... 562/521, 519

(56) References Cited

U.S. PATENT DOCUMENTS

| | | | |
|---|---|---|---|
| 3,036,124 | * | 5/1962 | John, Jr. . |
| 3,282,973 | * | 11/1966 | Devine et al. . |
| 3,923,880 | * | 12/1975 | Westlake et al. . |
| 4,652,677 | * | 3/1987 | Pesa et al. . |
| 5,241,112 | * | 8/1993 | Sanderson et al. . |
| 5,250,726 | * | 10/1993 | Burke . |
| 5,710,323 | * | 1/1998 | Okuda et al. . |

FOREIGN PATENT DOCUMENTS

| | | | |
|---|---|---|---|
| 0 249 976 A1 | * | 12/1987 | (EP) . |
| WO 92/18592 | * | 10/1992 | (WO) . |
| WO 96/20154 | * | 7/1996 | (WO) . |

OTHER PUBLICATIONS

*Advanced Organic Chemistry: Reactions, Mechanisms, and Structure*, Second Edition, Jerry March McGraw Hill International Book Company, p. 437.*

* cited by examiner

Primary Examiner—Gary Geist
Assistant Examiner—Leigh C. Maier

(57) ABSTRACT

A process for manufacture of branched carboxylic acids from branched olefins by means of reaction with carbon monoxide and a solid acid catalyst, characterized in that a branched olefin, or a precursor thereof, is reacted in a batch reactor or a plug flow reactor with carbon monoxide and water, in the presence of an acidic ion exchanger, having sufficient acid groups to provide requisite protons for conversion of said olefin or a precursor of it, and carbon monoxide into branched carboxylic acids, and in the presence of a polar non-coordinating organic solvent.

9 Claims, No Drawings

PROCESS FOR THE MANUFACTURE OF CARBOXYLIC ACIDS

FIELD OF THE INVENTION

The invention relates to a process for the manufacture of carboxylic acids. More in particular the invention relates to a process for the manufacture of branched carboxylic acids by means of a Koch synthesis using carbon monoxide as reagent and a solid acid catalyst.

BACKGROUND TO THE INVENTION

The up to now available processes are characterized by the fact that no solid acid catalyst could be used, unless said catalyst is operated under unattractively severe conditions or unless said catalyst is combined with corrosive Lewis acid cocatalyst or unless said catalyst is used in a non-aqueous reaction system.

In particular from International Application WO 96/20154 was known a process for the production of trialkylacetic acids from branched olefins and carbon monoxide in a non-aqueous reaction system using a solid resin catalyst comprising a cationic resin, having sufficient acid groups to provide requisite protons for conversion of branched olefin and carbon monoxide to trialkylacetic acids.

In particular the cationic resin was specified to have an acidity of at least equivalent to that of a 65 wt % sulphuric acid.

It will be appreciated by an average person skilled in the art that said process can only be performed in two steps, i.e. one step comprising contacting the solid catalyst with olefin/CO feed and a subsequent step contacting the catalyst with water feed, and that stoichiometric amounts of branched olefin and water will not lead to the desired products in an acceptable yield. Moreover, said process cannot produce more than 1 mole of converted olefin per mole active proton on the solid catalyst in one cycle of two steps.

On the other hand from WO 92/18592 was known a process for the manufacture of trialkylacetic acids and particularly of pivalic acid, from branched olefins and particularly isobutene, and Carbon monoxide, using a solid acid catalyst together with minor amounts of a Lewis acid, such as boron trifluoride.

In addition from EP-A-0249976 was known a process for the manufacture of branched carboxylic acids, by catalytic conversion of olefins with carbon monoxide and water in the presence of zeolites as catalysts at temperatures of from 200 to 500° C. and at pressures of 200 to 700 bar.

More in particular zeolites of the pentasil type are used as catalysts. According to the exemplified embodiments only high temperatures (300° C.) and pressures (300–500 bar) are used.

It will be appreciated that said disclosed reaction conditions will give rise to higher operation costs due to required measures as to safety and environment.

Therefore there is still a strong need for further improvement of the manufacturing process of branched carboxylic acids, starting from branched olefins and carbon monoxide.

An object of the present invention is providing an alternative efficient one step manufacturing process for branched carboxylic acids, which process uses relatively mild conditions on the one hand and which shows economically acceptable conversion and economically acceptable selectivity to branched acids on the other hand.

SUMMARY OF THE INVENTION

As a result of extensive research and experimentation there has now been surprisingly found a one step process for manufacture of branched carboxylic acids from branched olefins by means of reaction with carbon monoxide and a solid acid catalyst, characterized in that a branched olefin, or a precursor thereof, is reacted in a batch reactor or plug flow reactor with carbon monoxide and water, in the presence of an acidic ion exchanger, having sufficient acid groups to provide requisite protons for conversion of said olefin or a precursor of it, and carbon monoxide into branched carboxylic acids, and in the presence of a polar non-coordinating organic solvent.

More in particular the invention relates to an improved manufacturing process of trialkylacetic acids of the formula

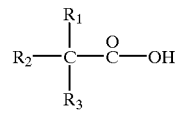

wherein each symbol R represents a radical having 1 to 10 carbon atoms.

More preferably the total number of carbon atoms in the trialkylacetic acids ranges from 5 to 19 and most preferably from 5 to 14 carbon atoms.

With the term "branched olefin or a precursor thereof" as used throughout the present specification is meant that branched olefin itself as well as alcohols, esters or ethers, from which the specific olefin can be easily derived, can be used as starting materials for the present manufacturing process, which makes this process much more flexible than conventional prior art processes. In general all olefins containing at least one tertiary carbon atom or precursors therefor, can be converted by the present process.

DESCRIPTION OF A PREFERRED EMBODIMENT

An important advantage of the present process is that it can be operated as one step or one reactor process showing an economically acceptable combination of conversion degree and selectivity.

The catalyst to be used for the process of the present invention is a solid acidic ion exchanger showing strong acid behavior. It is preferably selected from the group consisting of sulfonated resins and more preferably copolymers of styrene and divinylbenzene, phenol or phenolic based resins, sulfonated poly(tetrafluoroethylene) and sulfonated siloxane polymers.

In either case of the presence of active sulfonic acid groups, the resin is treated to give a sulfonic acid cation-exchange resin capable of providing sufficient protons, i.e. the resin having an acid strength equivalent to at least 65 wt % sulphuric acid and preferably to at least 70 wt % sulphuric acid.

Catalyst solid resins, comprising sulfonic acid groups and derived from copolymers from styrene, divinylbenzene and phenol or derived from (tetrafluoroethylene)polymers or from siloxane polymers are preferred.

Specific more preferred examples of commercial effective acidic catalysts are AMBERLYST, NAFION or DELOXAN catalysts (AMBERLYST, NAFION and DELOXAN are Trade Marks).

Most preferred are the NAFION type catalysts. More preferably NAFION NR50 catalyst is used. The reaction temperature in the batch reactor is in the range of from 25° C. to 200° C. and preferably from 100 to 150° C.

The pressure in the reactor is in the range of from 10 to 200 bar and preferably from 50 to 100 bar.

As polar non-coordinating organic solvents can be used chemically inert polar organic solvents such as carboxylic acids or derivatives thereof and more in particular esters, or an optionally substituted sulfolane (preferably sulfolane).

According to a more preferred embodiment of the present process, as polar non-coordinating solvent a branched acid is present in the reactor. Most preferably the carboxylic acid to be produced can be used as solvent.

Normally the reactor is filled with solvent and catalyst with a catalyst/solvent wt ratio of in the range of from 0.01 to 0.5 w/w and preferably 0.2–0.3 w/w. The other respective reactants are introduced into the reactor and reaction mixture is heated to the desired reaction temperature.

The feed of starting olefin is in the range of from 0.01 to 10 g/g catalyst and preferably from 0.2 to 5 g/g catalyst, while the water/olefin molar ratio is in the range of from 0.5 to 2 mole/mole and preferably about 1 and the CO/olefin molar ratio is in the range of from 0.5 to 1000 mole/mole and preferably from 1 to 100.

It will be appreciated that, when using water amounts significantly below the hereinbefore specified amounts, the process becomes unattractive due to too low selectivity and that the selectivity and conversion have surprisingly been improved when using stoichiometric water:olefin=1:1 feed.

The invention is further illustrated by the following examples, however without restricting its scope to these specific embodiments.

EXAMPLE 1

1.5 g of dried Amberlyst 15 (6 meq) were loaded in a 60 ml batch reactor dried for 2 hours at 150° C. under vacuo, suspended in a solution of 20 g of n-heptanoic acid (solvent), 2 g di-isobutylcarbinol (DIBC), which is to be regarded as olefin precursor and finally activated by heating up to 180° C. under 80 bar CO for 17.5 hrs.

Under these conditions, the reaction proceeded with about 98.8% conversion of DIBC and 26.6 mol % yield of the branched carboxylic acid having 10 carbon atoms (V10).

Comparative Example 1

When the experiment of example 1 was repeated using dodecane as solvent instead of n-heptanoic acid, the DIBC conversion amounted to 99.2 mol %, and 6.7 mol % yield of V10.

EXAMPLE 2

With the experiment of example 1 was repeated with 7 milliequivalent of NAFION NR50 (8.7 g) as catalyst instead of AMBERLYST 15, and a reaction temperature of 150 ° C. instead of 180°C., the DIBC conversion after 5 hours was 91% and the V10 yield was 28 mol %. After 17.5 hours the DIBC conversion was more than 99 mol % while the V10 yield amounted to 39 mol %.

Comparative Example 2

When the experiment of example 2 was repeated with using dodecane as solvent instead of n-heptanoic acid, the DIBC conversion amounted to 99 mol % and the yield in V10 did not exceed 1 mol % after 17.5 hours.

EXAMPLE 3

When the experiment of example 2 was repeated using pivalic acid in the same molar amount instead of n-heptanoic acid, the DIBC conversion was 99%, while the V10 yield amounted to 42 mol % after 5 hours.

Comparative Example 3

When the experiment of example 2 was repeated using dipentyl ether in the same molar amount instead of n-heptanoic acid, the DIBC conversion was 99%, while the V10 yield was only 0.4 mol % after 5 hours.

Comparative Examples 4–6

The experiment of example 2 was repeated and the n-heptanoic acid was replaced by the same weight amounts of, monoethylene glycol and diethylene glycol respectively, which disappeared due to significant interference with the reaction. No substantial V10 was formed.

We claim:

1. A process for manufacture of branched carboxylic acids from branched olefins by means of reaction with carbon monoxide and a solid acid catalyst, the process comprising the steps of:

reacting a branched olefin, or a precursor thereof, in a batch reactor or plug flow reactor with carbon monoxide and water, in the presence of an acid ion exchanger, having sufficient acid groups to provide requisite protons for conversion of said olefin or a precursor of it, and carbon monoxide into branched carboxylic acids, and in the presence of a organic solvent selected from the group consisting of sulfolane, carboxylic acids and esters; and recovering a branched carboxylic acid product.

2. The process of claim 1 wherein as solid acid catalyst is used a solid acidic ion exchanger, selected from the group consisting of sulfonated resins, sulfonated poly (tetrafluoroethylene) and sulfonated siloxane polymers.

3. The process of claim 2 characterized in that the resin is treated to give a sulfonic acid cation-exchange resin, such that the resin having an acid strength equivalent to at least 65 wt % sulfuric acid.

4. The process of claim 1 wherein the pressure in the reactor is in the range of from 50 to 100 bar.

5. The process of claim 1 wherein during the reaction a carboxylic acid or a derivative thereof is present as solvent in the reactor.

6. The process of claim 1 wherein the catalyst/solvent weight ratio is in the range of from 0.01 to 0.5 w/w.

7. The process of claim 1 wherein the feed of starting olefin is in the range of from 0.01 to 10 g/g catalyst.

8. The process of claim 1 wherein the water/olefin molar ratio is in the range of from 0.5 to 2 mole/mole.

9. The process of claim 1 wherein the CO/olefin molar ratio is in the range of from 0.5 to 1000 mole/mole.

* * * * *